(12) United States Patent
Schweitzer et al.

(10) Patent No.: US 7,058,212 B2
(45) Date of Patent: Jun. 6, 2006

(54) ARRANGEMENT AND METHOD FOR DETERMINING THE TWO-DIMENSIONAL DISTRIBUTION OF FUNDUS PIGMENTS, PARTICULARLY OF THE MACULAR PIGMENT XANTHOPHYLL

(75) Inventors: Dietrich Schweitzer, Neustadt/Orla (DE); Lutz Leistritz, Bucha (DE); Martin Hammer, Jena (DE); Karl-Heinz Donnerhacke, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 755 days.

(21) Appl. No.: 10/172,563

(22) Filed: Jun. 13, 2002

(65) Prior Publication Data
US 2002/0193948 A1    Dec. 19, 2002

(30) Foreign Application Priority Data
Jun. 15, 2001 (DE) .............................. 101 29 652

(51) Int. Cl.
*G06K 9/00* (2006.01)
(52) U.S. Cl. ....................................... 382/128; 348/78
(58) Field of Classification Search ................ 382/100, 382/117, 128; 348/78; 351/200, 205, 206
See application file for complete search history.

(56) References Cited

U.S. PATENT DOCUMENTS

| | | | | |
|---|---|---|---|---|
| 5,873,831 A * | 2/1999 | Bernstein et al. | ............ | 600/473 |
| 6,017,122 A * | 1/2000 | Bone et al. | .................. | 351/221 |
| 2003/0130579 A1* | 7/2003 | McClane et al. | ............ | 600/476 |

FOREIGN PATENT DOCUMENTS

| | | |
|---|---|---|
| DE | 197 20 851 A1 * | 11/1988 |
| DE | 197 33 995 A1 * | 2/1999 |

OTHER PUBLICATIONS van de Kraats et al., "The Pathways of Light Measured in Fundus Reflectometry," *Vision Res.*, vol. 36, No. 15, pp. 2229-2247, 1996.*

(Continued)

*Primary Examiner*—Andrew W. Johns
(74) *Attorney, Agent, or Firm*—Reed Smith LLP

(57) ABSTRACT

An arrangement and method for determining the two-dimensional distribution of fundus pigments, particularly of the xanthophyll macular pigment. The arrangement for carrying out the method comprises an illumination unit which illuminates the retina via an illumination beam path directed to the ocular fundus, observation optics located in the observation beam path proceeding from the ocular fundus, an image processing unit, elements for beam deflection and a central controlling and evaluating unit. In the method, a two-dimensional reflection image of the retina is recorded in a selected narrow-band wavelength region. In evaluating this two-dimensional reflection image, site-specific areas are established for determining the optical density and comparison values. The optical density of the fundus pigment at every fundus location is calculated from the negative logarithmic value of the quotient of the intensity value of the reflection image $I_{R(\lambda)}$ at this fundus site to a comparison intensity value of the reflection image $I_{R(\lambda) Comparison}$. The suggested solution for the objective detection of the two-dimensional distribution of the optical density of the macular pigment xanthophyll is also suitable in principle for determining the distribution of other fundus pigments.

11 Claims, 2 Drawing Sheets

OTHER PUBLICATIONS

Berendschot et al., "Influence of Lutein Supplementation on Macular Pigment, Assessed with Two Objective Techniques," *Investigative Ophthalmology & Vision Science*, Oct. 2000, vol. 41, No. 11, pp. 3322-3326.*

Chang et al., "Retinal macular pigment distribution measured by imaging fundus reflectometry," *Proc. SPIE vol. 4625: Clinical Diagnostic Systems: Technologies and Instrumentation*, Jan. 2002, pp. 170-178.*

* cited by examiner

US 7,058,212 B2

ARRANGEMENT AND METHOD FOR DETERMINING THE TWO-DIMENSIONAL DISTRIBUTION OF FUNDUS PIGMENTS, PARTICULARLY OF THE MACULAR PIGMENT XANTHOPHYLL

CROSS-REFERENCE TO RELATED APPLICATIONS

This application claims priority of German Application No. 101 29 652.5, filed Jun. 15, 2001, the complete disclosure of which is hereby incorporated by reference.

BACKGROUND OF THE INVENTION a) Field of the Invention

The present invention is directed to an arrangement and a method for determining the two-dimensional distribution of fundus pigments, particularly of the macular pigment xanthophyll. Xanthophyll has a positive effect on prevention of age-related macular degeneration (AMD), since, on the one hand, it is an absorber of high-energy short-wave radiation and therefore leads to reduced formation of free radicals and, on the other hand, is itself an effective radical scavenger. Therefore, it is presumed that a reduced optical density of xanthophyll represents an increased risk factor for incidence of AMD.

b) Description of the Related Art

According to the known prior art, there is a range of subjective and objective methods for determining the optical density of xanthophyll pigment in the macula.

In the flicker matching method of Bone and Hammond [1], local areas inside and outside the fovea are alternately irradiated by light of a suitable wavelength. The irradiation intensities are varied until the patient subjectively perceives the identical brightness. The optical density of the xanthophyll in the irradiated area of the macula can then be determined from the ratio of the foveal and parafoveal irradiation intensities. This method has the drawback that it can only provide locally defined information about the optical density. However, its decisive disadvantage consists in that it is a subjective method, i.e., it relies on the cooperation of the test subject. The method assumes the subject's capability for fixation and cooperation and therefore can be realized only with difficulty for the typically older patients and can not be carried out at all with subjects having foveal fixation loss (e.g., with AMD).

The known objective methods of fundus spectroscopy according to Berendschot, van der Kraats and Schweitzer [2] are based on the evaluation of the reflectance spectra in a selected retinal area or on the evaluation of difference spectra at two spatially separate (foveal, parafoveal) retinal areas. This method has the disadvantage that only pointwise local measurements or measurements only along a line are possible. Further, this method involves expensive apparatus and is therefore unsuitable for extensive practical application.

In the so-called two-wavelength method according to Elsner [3], reflection images of the retina are recorded by laser scanners in two different wavelengths and the absorption maximum of xanthophyll is determined by forming the quotient while taking into account the relative absorption proportions. While this objective measurement method makes it possible to determine the two-dimensional distribution of the optical density, the measurements can be falsified by the transparency of the front ocular media which varies depending upon wavelength.

Delori [4] describes another objective method in which it is possible, in principle, to detect the two-dimensional distribution by measuring the attenuation of the fluorescence intensity of submacular endogenous fluorophores. However, because of the very low autofluorescence intensity of endogenic fluorophores, expenditure on apparatus is extremely high. Further, the measurements can likewise be falsified by the varying transparency characteristics of the front ocular media.

LITERATURE

[1] Bone R A, Landrum J T, Kilburn M D, Gomez C, "Effect of dietary supplementation with lutein on macular pigment density", (1996) *Invest Ophthalmol Vis. Sci.* 37 (3): 112

Hammond B R, Johnson E J, Russell R M, Krinski N I, Yeum K J, Edwards R B, Snodderly D M, "Dietary modification of human macular pigment density", (1997) *Invest Ophthalmol Vis. Sci.* 38 (9): 1795–1801

[2] van der Kraats J, Berendschot T T J M, van Norren D, "The pathways of light measured in fundus reflectometry", (1996) *Vision Res.* 36: 2229–2247

Berendschot T T J M, Goldbohm R A, Klöpping W A A, van der Kraats J, van Norel J, van Norren D, "Influence of lutein supplementation on macular pigment, assessed with two objective techniques", (2000) *Invest Ophthalmol Vis. Sci.* 41: 3322–3326

Schweitzer D, Tröger G, Königsdörffer E, Klein S, "Multisubstanzanalyse Nachweis von Änderungen der optischen Dichte in einzelnen Schichten des Augenhintergrundes [Multisubstance analysis detection of changes in optical density in individual layers of the ocular fundus]", (1991) *Fortschr. Ophthalmol.* 88: 554–561

Schweitzer D, Hammer M, Scibor M, Leistritz L, "Confocal imaging spectrometry of the human fundus", (1998) *Laser and Light* 8: 153–160

[3] Elsner A E, Burns S A, Delori F C, Webb R H, "Quantitative reflectometry with the SLO", (1990) in Nasemann J E, Burk R O W, eds., Laser Scanning Ophthalmoscopy and Tomography, Munich, Quintessenz-Verlag 1990: 109–121

[4] Delori F C, Goger D G, Hammond B R, Snodderly D M, Burns S A, "Foveal lipofuscin and macular pigment", (1997) *Invest Ophthalmol Vis. Sci.* March 15, Vol. 38, No. 4, page 355

[5] Leistritz L, Schweitzer D, "Shading correction in retinal images", SPIE Vol. 2298, 692–696

[6] Rassow B, et al., "Ophthalmologisch-optische Instrumente [Ophthalmologic-optical instruments]", Bücherei des Augenarztes, Vol. 111, Ferdinand Enke Verlag, Stuttgart 1987, 182–187

The solutions known from the prior art have the disadvantages that the measurements can be falsified either by subjective influences or by wavelength-dependent differences in transparency of the front ocular media, or that extensive applicability is prevented by complicated and costly apparatus.

OBJECT AND SUMMARY OF THE INVENTION

Therefore, it is the primary object of the present invention to develop an objective method, and a suitably simple arrangement for implementing this method, for detecting the two-dimensional distribution of the optical density of fundus pigments, particularly of the macular pigment xanthophyll.

According to the invention, this object is met by the arrangement and the method in that, after the recording of a two-dimensional reflection image of the retina with illumination by narrow-band light, site-specific areas are established for determining the optical density of the respective fundus pigment and the comparison values. The optical density of the fundus pigment at every fundus site is given by the negative logarithmic value of the quotient of the intensity value of the reflection image $I_{R(\lambda)}$ at this fundus site to a comparison intensity value of the reflection image $I_{R(\lambda)Comparison}$.

The suggested solution for objective detection of the two-dimensional distribution of the optical density of fundus pigments is not only suitable for determining the distribution of the macular pigment xanthophyll.

The invention will be described more fully in the following with reference to an embodiment example.

DESCRIPTION OF THE PREFERRED EMBODIMENTS

Figure 1:
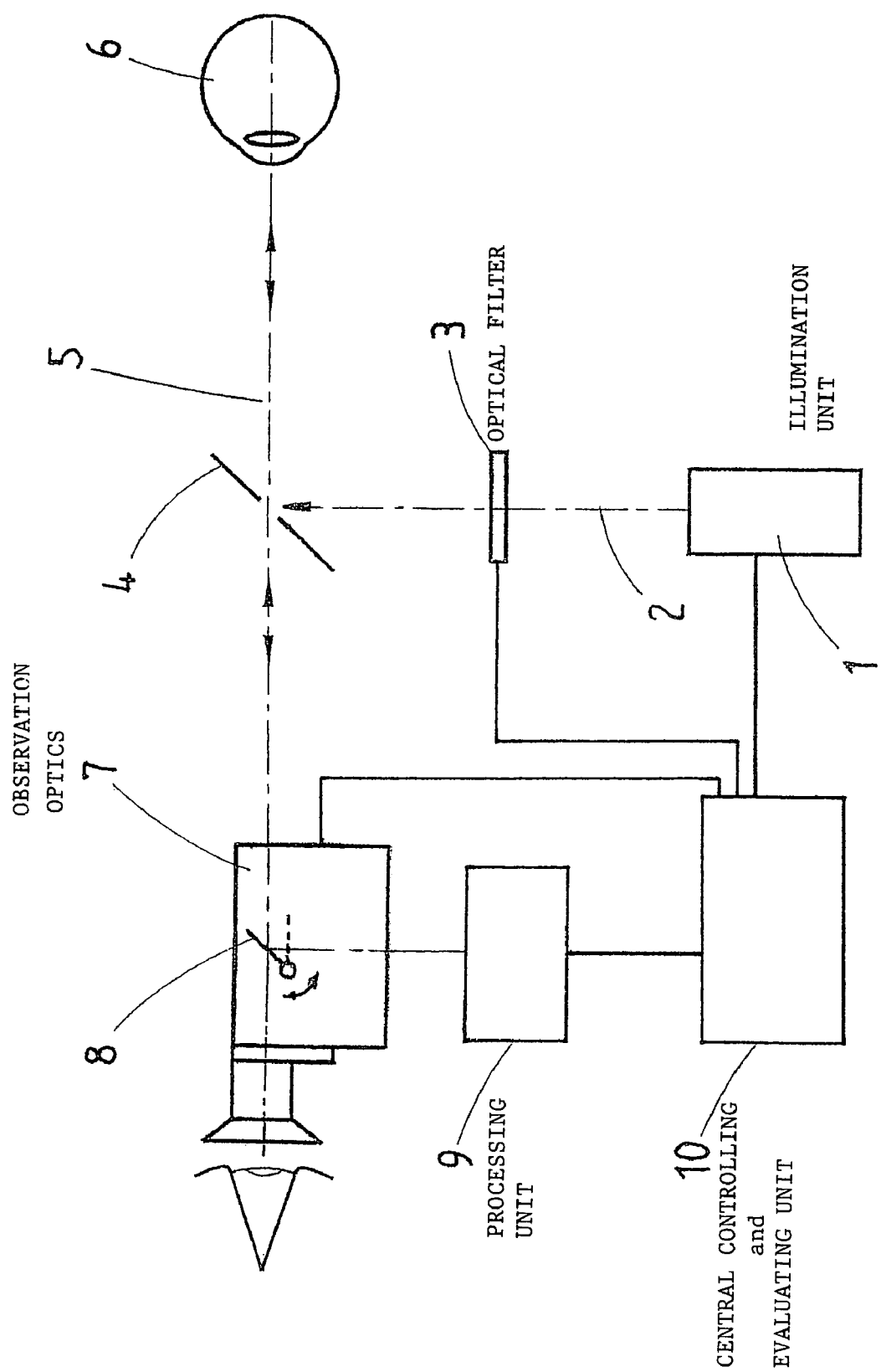
FIG. 1 shows a possible arrangement for carrying out the method.

In the method to be carried out by means of the arrangement according to FIG. 1, the eye of the subject 6 is first irradiated by light by means of the illumination unit 1. Proceeding from the illumination unit 1, the light reaches the eye of the subject 6 through the optical filter 3 arranged in the illumination beam path 2 and the perforated mirror 4 used for coupling into the observation beam path 5. The optical filter 3 is transparent for a narrow-band wavelength range with a mean or center wavelength of $\lambda=460$ nm which corresponds to the absorption maximum of xanthophyll. However, the optical filter 3 can be dispensed with when the illumination device 1 emits monochromatic light in the selected narrow-band wavelength range. The observation optics 7 serve for exact orientation of the arrangement. Subsequently, a two-dimensional reflection image of the retina of the subject is recorded by the image recording and processing unit 9 and is processed and conveyed to the central controlling and evaluating unit 10. For this purpose, the swing-out mirror 8 arranged in the observation optics is swiveled into the observation beam path 5.

Figure 2:
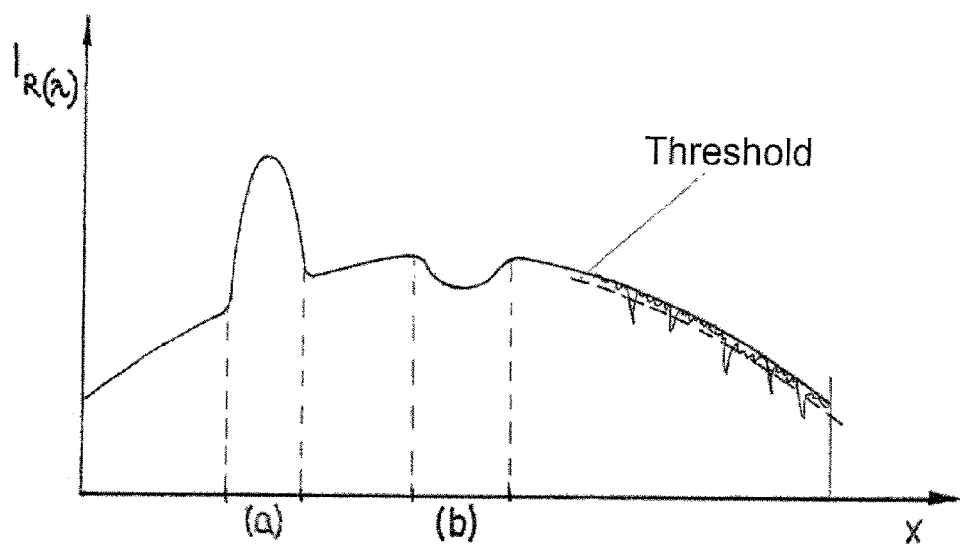
FIG. 2 shows the intensity distribution for the reflection in a selected wavelength region.

FIG. 2 shows the intensity distribution $I_{R(\lambda)}$ resulting from the reflection image. The characteristic intensity peak (a) occurs in the area of the papilla. The characteristic intensity drop (b) is brought about by the area of the macula.

In another method step, by evaluating this reflection image, the central controlling and evaluating unit 10 determines site-specific comparison values from retinal areas in which no xanthophyll is detectable. The central controlling and evaluating unit 10 implements all determination, evaluation and display. The optical density of the xanthophyll is given by the negative logarithmic value of the quotient of the intensity value of the reflection image $I_{R(\lambda)}$ at this fundus site in the area of the macula to a comparison intensity value of the reflection image $I_{R(\lambda)Comparison}$.

$$OD=-\log(I_{R(\lambda)}/I_{R(\lambda)Comparison})$$

In a refinement of the method, uneven illumination of the ocular fundus can also be taken into account (shading correction). The required reference points or grid points for the illumination function are determined from structureless areas. The method indicated in [5] can be used to calculate the illumination function in the image plane. This function characterizes the illumination of the ocular fundus with high accuracy, particularly in the area of the macula. As is shown in FIG. 2, a threshold value is determined after the shading correction is carried out. The measurements are accordingly not falsified by spectral interference and general noise. The optical density OD of the distribution of the xanthophyll in the area of the macula is given by the negative logarithmic value of the quotient of the intensity value of the reflection image $I_{R(\lambda)}$ at this fundus site to the corresponding intensity value of the shading correction $I_{Shading(\lambda)}$ at the same fundus site.

$$OD=-\log(I_{R(\lambda)}/I_{Shading(\lambda)})$$

Figure 4:
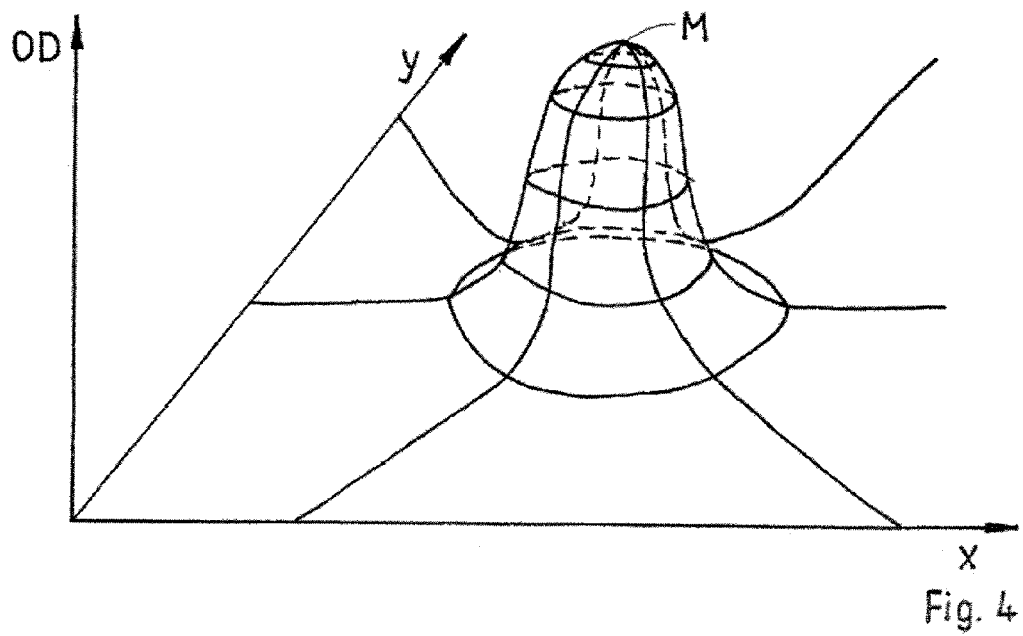
FIG. 4 shows an absorption profile of the optical density OD.

In the subsequent method step, the optical density OD at every fundus site is displayed as a color-coded two-dimensional absorption profile. FIG. 4 shows a two-dimensional distribution of the optical density of xanthophyll with a maximum value M. Errors which may occur when there is an asymmetric distribution of the xanthophyll in which the maximum optical density is localized outside the fovea are avoided in particular by evaluating the following evaluation parameters: area F, volume V and maximum value M of the absorption profile.

Figure 3:
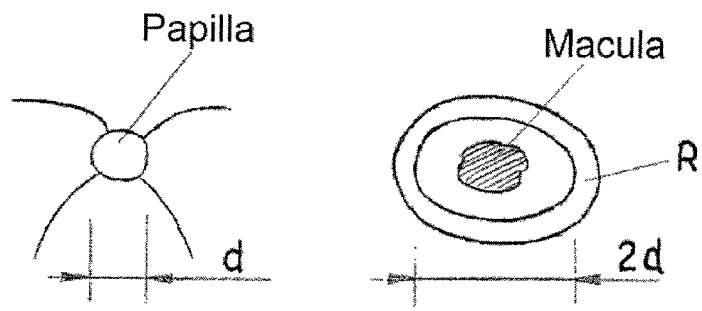
FIG. 3 shows the annular area to be determined in method step 8.

In most cases, it is sufficient that only one comparison value is determined by the central controlling and evaluating unit 10 by evaluating the reflection image in a ring-shaped area surrounding the macula with a diameter of about 2 papilla diameters d as a mean value for the intensity of the comparison sites. In this connection, FIG. 3 shows the ring-shaped area R to be determined around the macula. The width of this area R corresponds to at least one pixel width.

An objective detection of the two-dimensional distribution of the optical density of fundus pigments, particularly of the macular pigment xanthophyll, is made possible in a simple manner by the method according to the invention and the arrangement suitable for implementing this method. The method is suitable for all known instruments for examination of the ocular fundus which enable a narrow-band illumination of the fundus and which have an image recording unit. The central controlling and evaluating unit 10 can be connected to this image recording unit to determine, evaluate and display the corresponding measured values.

Accordingly, it is also possible to use ophthalmologic examination instruments (e.g., according to DE-OS 197 20 851 A1) or special laser scanning ophthalmoscopes (e.g., according to DE-OS 197 33 995 A1). Possible fundus cameras which are also suitable are described in [6].

While the foregoing description and drawings represent the present invention, it will be obvious to those skilled in the art that various changes may be made therein without departing from the true spirit and scope of the present invention.

What is claimed is:

1. An arrangement for determining the two-dimensional distribution of fundus pigments, particularly of the macular pigment xanthophyll, comprising:

a unit for a single monochromatic illumination or a unit with an optical filter arranged in front of it being provided for a single narrow-band illumination of the retina with light of a wavelength region containing precisely or approximately the wavelength λ of the absorption maximum of the fundus pigment;

image processing unit for recording and evaluating the image reflected by the retina being arranged in an extended observation beam path; and a central controlling and evaluating unit being provided for selecting site-specific areas for the optical density to be determined and for the selection and calculation of reference values and for determining the optical density of the respective fundus pigment and for numerical or graphic output of the results, wherein said central controlling and evaluating unit being connected with the illumination unit, the filter, observation optics and the image processing unit.

2. The arrangement according to claim 1, wherein the monochromatic illumination unit emits a single narrow-band light of a center wavelength of λ=460 nm, which corresponds to the absorption maximum of xanthophyll, or in that the optical filter is transparent only for a single narrow-band light around the center wavelength of λ=460 nm.

3. A method for determining a two-dimensional distribution of fundus pigments, particularly of the macular pigment xanthophyll, particularly by operation of an arrangement according to claim 1, comprising the steps of:

a first method step for recording and processing a two-dimensional image of the retina with illumination by a single narrow-band light, in whose spectral range the respective fundus pigment absorbs;

a second method step for selecting site-specific areas for determining the optical density of the respective fundus pigment and for selecting site-specific areas for determining the reference values;

a third method step for calculating the optical density of the fundus location from the negative logarithmic value of the quotient of the intensity value of the reflection image $I_{R(\lambda)}$ at this fundus site to a comparison intensity value of the reflection image $I_{R(\lambda)Comparison}$ and outputting said optical density—as a two-dimensional image.

4. The method according to claim 3, wherein in a first method step a two-dimensional image of the retina is recorded with illumination by the single narrow-band light, in whose spectral range the fundus pigment xanthophyll absorbs, and is processed, wherein in a second method step site-specific areas for the optical density of the respective fundus pigment xanthophyll to be determined and the reference values are determined, wherein in a third method step the optical density of the fundus pigment xanthophyll in the area of the macula is calculated from the negative logarithmic value of the quotient of the intensity value of the reflection image $I_{R(\lambda)}$ at this fundus site to a comparison intensity value of the reflection image $I_{R(\lambda)Comparison}$ and outputting said optical density as a two-dimensional image.

5. The method according to claim 4, wherein a comparison intensity value is selected from only one individual fundus site outside the macular absorption area of the fundus pigment xanthophyll at a distance of approximately one papilla diameter from the fovea, or wherein the comparison intensity value is formed as an average intensity from an annulus around the macula with a diameter of approximately two papilla diameters and a width of at least one pixel, or wherein the comparison intensity values are determined individually for every fundus site at which the optical density of the fundus pigment xanthophyll is to be determined by a simulation which takes into account the illumination of the ocular fundus.

6. The method according to claim 3, wherein a comparison intensity value is selected from only one individual fundus site outside the absorption range of the respective fundus pigment, or wherein the comparison intensity value is formed as an average intensity from an annulus with a diameter of approximately two papilla diameters and a width of at least one pixel, or wherein the comparison intensity values are determined individually for every fundus site at which the optical density of the respective fundus pigment is to be determined by means of a simulation which takes into account the illumination of the ocular fundus.

7. The method according to claim 6, wherein a comparison intensity value is selected from only one individual fundus site outside the macular absorption area of the fundus pigment xanthophyll at a distance of approximately one papilla diameter from the fovea, or wherein the comparison intensity value is formed as an average intensity from an annulus around the macula with a diameter of approximately two papilla diameters and a width of at least one pixel, or wherein the comparison intensity values are determined individually for every fundus site at which the optical density of the fundus pigment xanthophyll is to be determined by a simulation which takes into account the illumination of the ocular fundus.

8. The method according to claim 6, wherein grid points from structureless site-specific areas are used for the calculation of the illumination function.

9. The method according to claim 3, wherein a threshold value is determined in order to obtain measurement values which are not falsified by spectral interference and/or general noise.

10. The method according to claim 3, wherein, in addition to the optical density, the evaluation parameters comprising area, volume and maximum value of the absorption profile are determined.

11. The method according to claim 3, wherein the distribution of the optical density is determined and displayed in the form of a two-dimensional false color display, and wherein the determined evaluation parameters of surface, volume and maximum value of the absorption profile are included in the display.

* * * * *